United States Patent [19]

Cheslow

[11] 3,970,086

[45] July 20, 1976

[54] DISPOSABLE DIAPER HAVING TAB FASTENING MEANS WITH ONE END THEREOF RELEASABLY ADHERED TO DIAPER

[75] Inventor: Ernest Cheslow, Glencoe, Ill.

[73] Assignee: Johnson & Johnson, New Brunswick, N.J.

[22] Filed: May 7, 1975

[21] Appl. No.: 575,281

[52] U.S. Cl. ............................... 128/287; 128/284
[51] Int. Cl.² .......................................... A61F 13/16
[58] Field of Search ............... 128/284, 287, 290 R; 24/67

[56] References Cited
UNITED STATES PATENTS

| 3,620,217 | 11/1971 | Gellert | 128/284 |
| 3,642,001 | 2/1972 | Sabee | 128/287 |
| 3,646,937 | 3/1972 | Gellert | 128/287 |
| 3,875,621 | 4/1975 | Karami | 24/67 |
| 3,880,165 | 4/1975 | Prizzia | 128/284 |

*Primary Examiner*—Aldrich F. Medbery

[57] ABSTRACT

A disposable diaper is provided with adhesive tabs, each having an adhesive surface on one face, and further having a fixed end permanently adhered to a backing sheet of the diaper at a marginal location, and a working end. A cover strip means is releasably adhered to the adhesive surface on the working end of each tab. Between the face opposite the adhesive surface on the working end of each tab and the backing sheet is positioned an adhesive spot so that the working end is releasably adhered to an intermediate portion of the backing sheet when the diaper is prefolded in a box pleat configuration and when the working end is folded over during manufacture or packaging.

8 Claims, 3 Drawing Figures

U.S. Patent  July 20, 1976  3,970,086
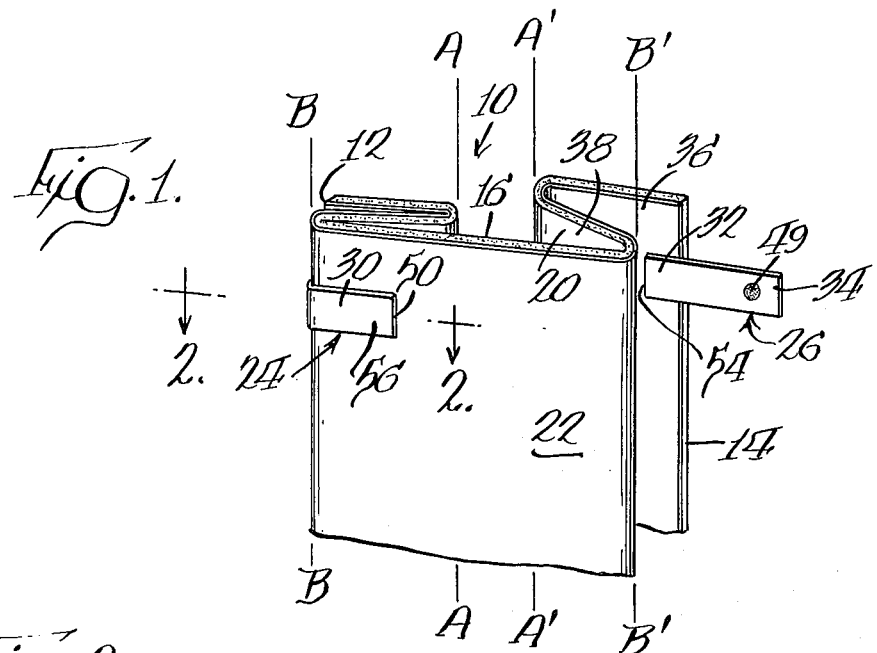
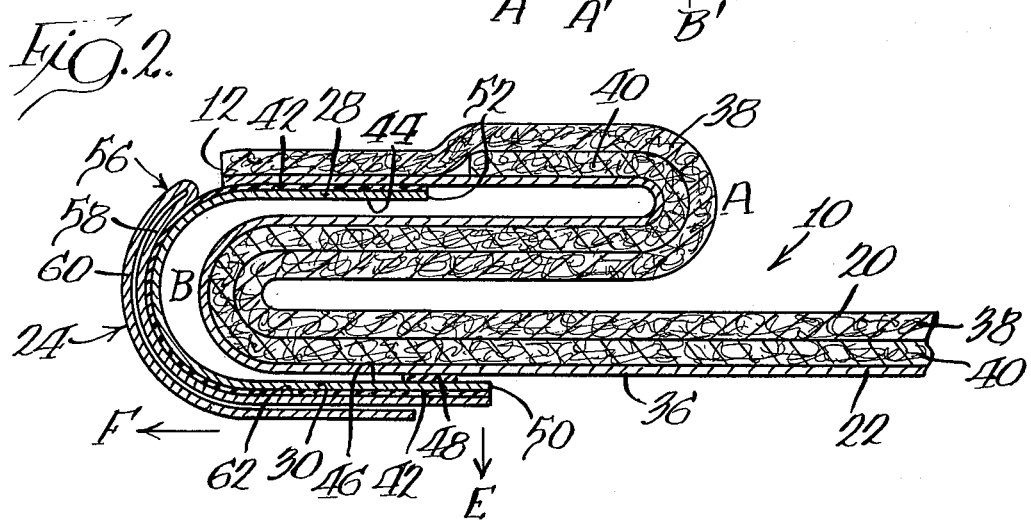
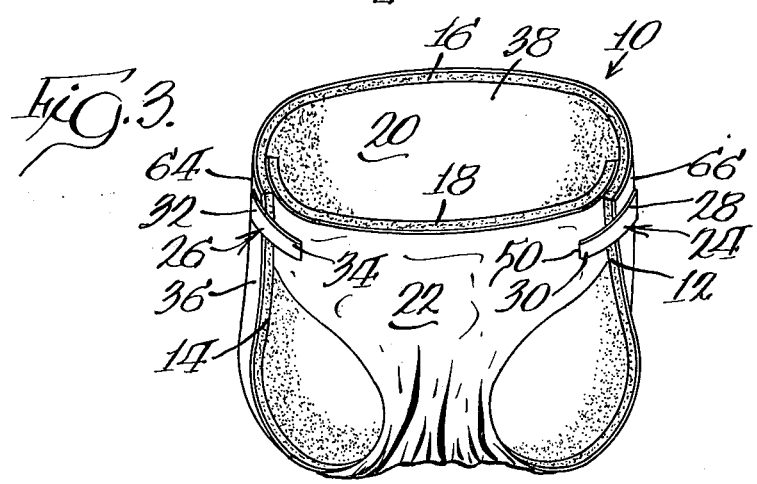

DISPOSABLE DIAPER HAVING TAB FASTENING MEANS WITH ONE END THEREOF RELEASABLY ADHERED TO DIAPER

BACKGROUND OF THE INVENTION

Disposable diapers provide substantial advantages in convenience over diapers intended to be laundered and reused, particularly when the diapers are used away from home. In recent years, many different disposable diapers have been proposed and some have been successful in the marketplace. Typical disposable diaper structures comprise a facing material to be brought into contact with the infant's skin, an absorptive moisture-retaining layer of relativey high moisture-holding capacity, and a moisture-impervious backing sheet. Typical disposable diaper structures are shown in U.S. Pat. No. 3,612,055 to Mesek et al., and in U.S. Pat. No. Re. 26,151 to Duncan et al.

As may be seen from the above-cited patents, it has been desirable to obviate the problems that are inherent in closure systems utilizng extraneous fasteners such as safety pins, snaps and zippers, and tab-type adhesive closure systems have been used in lieu of such extraneous fasteners.

The adhesive systems shown in the above-mentioned patents include adhesive tabs which are adhered to the backing sheet and which extend outwardly from opposite sides of the diaper at one end thereof. The exposed areas of the adhesive tabs are provided with cover strips thereon that are readily separable from the adhesive tabs. One problem with disposable diapers using an adhesive closure system of this general type is that while one end of each adhesive tab is attached to the diaper the opposite end is free and can become entangled in the machinery used to manufacture or package the diapers, particularly in instances where the free end is relatively long.

SUMMARY OF THE INVENTION

In this invention, a disposable diaper, having a moisture-impermeable backing sheet forming a diaper outside surface for direction away from an infant when worn by that infant, a moisture-retaining layer adhered to the backing sheet, and a facing sheet which forms a diaper inside surface for direction toward an infant, has a tab fastener means having a fixed end permanently adhered to the diaper backing sheet at a marginal location, and a free working end with a layer of pressure-sensitive adhesive facing in the same direction as the diaper inside surface. A cover strip means is releasably adhered to the adhesive surface on the working end of the tab. The opposite face on the working end of the tab has an adhesive spot thereon. Alternatively, an adhesive spot can be provided on an intermediate portion of the diaper backing sheet for the purpose of temporarily securing the free working end thereto, or complementary spots of a contact adhesive can be provided on both the free working end and the diaper backing sheet.

A marginal portion along each lateral edge of the diaper is folded inwardly about a first fold line, such that the outside surface of the diaper is juxtaposed to itself. Each side of the diaper is again folded longitudinally about a second fold line disposed in an intermediate portion of the diaper, inwardly of the first fold line, but usually at a distance less than one-fourth of the transverse distance between the first fold lines, such that the inside surface of the diaper is juxtaposed to itself on both sides of the second fold line, and the diaper is in a box pleat configuration.

When the diaper is in the box pleat configuration the fixed end of each tab is disposed within the first fold. The working end of each tab is folded back about the second fold line, and the adhesive spot enables the working end to be releasably adhered to the diaper backing sheet at a location inwardly of the second fold line. The working end of the tab is thereby releasably attached to the diaper where it will not interfere with machinery during the manufacturing process. The cover strip which is releasably adhered to the working end of the tab is provided with a gripping means, whereby a user can pull the cover strip outwardly to separate the working end of the tab from the diaper backing sheet, and peel the cover strip from the tab to expose the adhesive when applying the diaper to an infant.

BRIEF DESCRIPTION OF THE DRAWING

In the drawings,

FIG. 1 is a fragmentary perspective view of a disposable diaper embodying the present invention;

FIG. 2 is an enlarged fragmentary cross-sectional elevation taken along plane 2—2 in FIG. 1; and FIG. 3 is a perspective view of a disposable diaper embodying the present invention shown in a configuration assumed by the diaper when placed about an infant.

DESCRIPTION OF THE PREFERRED EMBODIMENTS

Referring to FIGS. 1, 2 and 3, disposable diaper 10, having a substantially rectangular configuration with lateral edges 12 and 14 and transverse edges 16 and 18, and presenting inside surface 20 for direction toward an infant and outside surface 22 for direction away from the infant, is provided with adhesive tabs 24 and 26 which can be made of polyethylene sheet, polypropylene sheet, or similar materials. As illustrated by tab 24, the tab fastening means comprises fixed end 28 and working end 30. Similarly, tab 26 is provided with fixed end 32 and working end 34. Tabs 24 and 26 are attached to diaper 10 by securing fixed ends 28 and 32 to diaper backing sheet 36. The moisture-retaining layer of diaper 10 comprises liquid-pervious facing sheet 38 and absorbent pad 40 which is situated between facing sheet 38 and backing sheet 36.

As best illustrated in FIG. 2, fixed end 28 is permanently secured to outside surface 22 of backing sheet 36 at a marginal location along lateral edge 12 by means of pressure-sensitive adhesive layer 42 provided on one face of the substrate of tab fastener 24. Alternatively, in instances where the tab fastener and the backing sheet both are made of a thermoplastic material, fixed end 28 can be secured to backing sheet 36 by heat bonding, and adhesive layer 42 is coextensive only with working end 30 in such an instance.

Working end 30 of tab 24 is adapted to extend beyond the perimetric limits of diaper 10, and has one face bearing a tacky, pressure-sensitive adhesive layer 42, and an opposite face 46 bearing adhesive layer 48 thereon. Adhesive layer 48 is preferably a spot near distal end 50 of working end 30 and preferably covers a minor portion of face 46 of working end 30. Adhesive spot 49 on opposite face 47 of working end 34 of tab 26 is illustrated in FIG. 1. Inasmuch as adhesive layer or spot 48 is situated between working end 30 and backing sheet 36, it is not critical whether the spot is more firmly anchored to working end 30 or backing sheet 36. Moreover, adhesive spot 48 can comprise two juxtaposed layers of a contact adhesive the adhesively active surface of which adheres only to itself so that the adhesively active surfaces will not pick up lint, or the like, when exposed while the diaper is being used.

For storage purposes, diaper 10 is prefolded during manufacture, such that diaper 10 is folded longitudinally and the fixed ends 28 and 32 of tabs 24 and 26 are situated within the resulting folds. A marginal portion along each lateral edge 12 and 14 of the diaper has a first fold about lines A—A and A'—A', respectively, said first fold lines being positioned inwardly of the distal ends 52 and 54 of fixed ends 28 and 32 of tabs 24 and 26, such that outside surface 22 is juxtaposed to itself along a marginal portion along each lateral edge of the diaper. Disposed in an intermediate portion of the diaper, inwardly of first fold lines A—A and A'—A', but less than one-fourth of the transverse distance between the first fold lines, are second fold lines B—B and B'—B', about which the diaper is further folded about itself with inside surface 20 juxtaposed to itself. FIG. 1 illustrates a portion of the folded diaper in a box pleat configuration. Diaper 10 can be packaged and stored in the box pleat configuration until ready for use.

It is recognized that the same result can be achieved by changing the order of the folding operations. Thus, different folding sequences are not critical for the purposes of the present invention.

As shown in FIGS. 1 and 2, when diaper 10 is in the box pleat configuration, first fold lines A—A and A'—A' are disposed inwardly from lateral edges 12 and 14, and second fold lines B—B and B'—B' are disposed inwardly from first fold lines A—A and A'—A' and lie in a plane substantially parallel to the diaper. As best illustrated in FIG. 2, fixed end 28 of tab 24 is juxtaposed to outside surface 22 between first fold line A—A and second fold line B—B. Working end 30 of tab 24 is folded about fold line B—B and adhesive spot 48 is juxtaposed to an intermediate portion of backing sheet 36 to which it is releasably adhered at a location between fold lines B—B and B'—B'. Adhesive spot 48 on working end 30 is releasably adhered to backing sheet 36 inwardly of second fold line B—B a distance approximately equal to the distance between adhesive spot 48 and lateral edge 12 when tab 24 is outstretched, although the actual thickness of the diaper and the positioning of the fold lines will somewhat affect this distance. The exact location of the intermediate area on backing sheet 36 to which adhesive tab 24 is releasably adhered is not critical to this invention.

Cover strip means 56 is releasably adhered to adhesive layer 42 on working end 30 of tab 24. Cover strip 56 can be folded back on itself providing gripping portion 60 which is juxtaposed in the folded configuration to working portion 58 which covers the tacky surface of working end 30, as illustrated in FIG. 2.

To expose adhesive layer 42 along working end 30 of tab 24, a user can first grasp working end 30, preferably along a corner at distal end 50, and pull upwardly in the direction of arrow E (FIG. 2) to separate working end 30 of tab 24 from the diaper outside surface 22 to which it was releasably adhered by adhesive spot 48. The user can then grasp gripping portion 60 of cover strip 56, and pull outwardly in the direction of arrow F, whereby working portion 58 of cover strip 56 will separate from working end 30 of tab 24, thereby exposing adhesive layer 42 which is adhesively fixed in a desired position on backing sheet 36 when applying the diaper to an infant.

A suitable backing sheet for the diaper embodying the present invention can be an opaque polyethylene web about 0.001 inch thick. Another suitable sheet material for this purpose is a polyethylene terephthalate web having a thickness of about 0.0005 inch.

Several different types of facing materials may be used for diaper facing sheet 38. For example, facing sheet 38 may be made up of a mixture of fibers consisting predominantly of inexpensive short cellulosic fibers, such as wood pulp fibers or cotton linters, in amounts of about 75% to about 98%, the balance being textile length fibers such as rayon as described in U.S. Pat. No. 3,663,348 to Liloia et al.

Facing sheet materials suitable for use in this invention have fabric weights in the range of about 1 to 5 oz./yd.$^2$ and densities of less than 0.15 g./cc., generally in the range between 0.05 and 0.1 g./cc. The dry strength of the facing sheet for a fabric having a weight of about 1.5 oz./yd.$^2$, is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 38 may also be made of an apertured, nonwoven fabric which is formed, for example, in accordance with the teachings in commonly assigned U.S. Pat. Nos. 2,862,251; 3,081,514; and 3,081,515. Briefly, such fabrics are foraminous structures wherein groups or groupings of fibers have been arranged from a fibrous nonwoven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers or blends thereof. Typical facing layers made of a polyester-type material can have a weight of ¾ oz./yd.$^2$.

In addition, facing sheet 38 can be formed of a non-apertured but fluid permeable material, such as a nonwoven isotropic web, sponge, or the like. In all of the aforementioned facings, the materials should be relatively hydrophobic so as to retard wicking within the facing layer.

Highly moisture-absorbent fibrous pad or batt 40 which is substantially rectangular in shape, but smaller than the facing and backing sheet, is centrally disposed therebetween. Pad 40 can be formed in accordance with the teachings of U.S. Pat. No. 3,612,055 to Mesek et al. Alternatively, a higher moisture-absorbent layer can be provided substantially coextensive with backing sheet 36 if desired.

Typical disposable diapers which can be fitted with a tab-type fastener described hereinabove are shown in U.S. Pat. No. 3,612,055 to Mesek et al. and in U.S. Pat. No. 3,683,916 to Mesek et al. Other suitable disposable diaper structures are shown in U.S. Pat. No. Re. 26,151 to Duncan et al.

Release properties can be imparted to working portion 58 of cover strip 56 by coating surface 62 thereof with a silicone release compound, or the like, or cover strip 56 may comprise a sheet of suitable release paper or a tape segment having an appropriate release surface.

Pressure-sensitive adhesive layers, such as layer 42, are provided by applying a pressure-sensitive adhesive known in the art. The applied adhesive shall have good tack, good cohesive strength, good resistance to moisture and good resistance to aging. Illustrative of such adhesives are mixtures of natural or synthetic rubber, zinc oxide, and various resins, also latices of natural or synthetic rubber, or water dispersions of acrylic tacky polymers or copolymers.

In use, a diaper equipped with the fasteners of this invention is applied to the infant by laying out the diaper on a suitable flat surface and placing the infant thereon so that the waist-underlying end of the diaper is that having the tab fastener means. The other end of the diaper then extends downwardly between the infant's legs. Next, the downwardly-extending end of the diaper is brought up between the infant's legs to a position contiguous with the front of the infant's waist. The tab is separated from the outside surface 22 of the diaper by pulling upwardly in the direction of arrow E. The diaper is thereafter secured to the infant by placing the corners of the waist portion of the abdomen-covering end as far around the infant's waist as they will go and by bringing corners 64 and 66 of the underlying end of the diaper into an overlapping relationship with the aforementioned corners so that the diaper snugly encirles the infant's waist. The overlapping corners, i.e., corners 64 and 66 in FIG. 3, are then folded back, peeling the corresponding cover strips from working ends 30 and 34 which are then adhesively fixed in a desired position on backing sheet 36 of the abdomen-covering end by simply urging the respective pressure-sensitive adhesive surfaces into contact therewith.

The foregoing description and the drawing are illustrative but are not to be taken as limiting. Still other variations and modifications are possible without departing from the spirit and scope of the present invention.

I claim:

1. A disposable diaper which comprises a moisture-impermeable backing sheet forming a diaper outside surface for direction away from an infant when the diaper is worn by that infant, a moisture-retaining layer adhered to the backing sheet and having a facing which forms a diaper inside surface for direction toward the infant, tab fastener means having a fixed end permanently secured to said diaper backing sheet and a working end folded back against said diaper backing sheet and provided with a pressure-sensitive adhesive presenting a tacky surface facing in the same direction as the diaper inside surface, a cover strip means releasably adhered to said tacky surface, and an adhesive spot between the diaper backing sheet and the face of the working end opposite said tacky surface which adhesive spot abuts said diaper outside surface, whereby said working end of said tab fastener means is releasably adhered to said diaper backing sheet on the diaper outside surface.

2. A disposable diaper as defined in claim 1 wherein said adhesive spot is positioned at the distal end of said face on said working end.

3. A disposable diaper as defined in claim 1 wherein said adhesive spot covers a minor portion of said face on said working end.

4. A disposable diaper as defined in claim 1 wherein said diaper has lateral and transverse edges and is prefolded with a first fold by folding a marginal portion of said diaper along each lateral edge over upon itself so that said outside surface is juxtaposed to itself and with a second fold by folding an intermediate portion which is situated inwardly of said marginal portion of said diaper laterally so that said inside surface is juxtaposed to itself on each side of said second fold, and wherein said working end of said tab fastener means is releasably secured to the intermediate portion of said diaper outside surface.

5. A disposable diaper as defined in claim 1 wherein said cover strip means is folded over upon itself and has a covering portion releasably secured to the tacky surface on said working portion of said tab fastening means, and a gripping portion adapted to be gripped by a user, said fold being positioned at the end of said working end of said tab fastening means which is opposite to the distal end of said working end of said tab fastening means.

6. In the method of manufacturing a disposable diaper in which a moisture-retaining layer is sandwiched between a moisture-impermeable backing sheet forming a diaper outside surface and a moisture-permeable facing layer forming a diaper inside surface and in which tab fasteners, each having a fixed end and a working end, are attached to edge portions of said backing sheet with their working ends extending beyond the edges at which they are attached, each of said adhesive tabs comprising a substrate and a tacky layer and having a release cover over said tacky layer at said working end, the improvement which comprises folding back the working ends of each of said adhesive tabs to bring a portion of said release cover into contact with a portion of said diaper backing sheet on said diaper outside surface and releasably attaching said portion of said release cover to said portion of said backing sheet.

7. In the method as defined in claim 6, providing an adhesive spot between said portion of said release cover and said portion of said diaper backing sheet to releasably attach said portion of said release cover to said portion of said backing sheet.

8. In the method as defined in claim 6, the further improvement comprising first folding marginal portions of said diaper over upon itself along a first fold line parallel to each lateral edge of said diaper so that said diaper outside surface is juxtaposed to itself, secondly folding intermediate portions of said diaper, situated inwardly of each of said marginal portions, along a second fold line parallel to each lateral edge and situated inwardly of said first fold line so that said diaper inside surface is juxtaposed to itself on each side of said second fold, and thereafter releasably attaching said folded back working end of each said adhesive tab to a portion of said diaper backing sheet disposed between said second folds.

* * * * *

Disclaimer

3,970,086.—*Ernest Cheslow*, Glencoe, Ill. DISPOSABLE DIAPER HAVING TAB FASTENING MEANS WITH ONE END THEREOF RELEASABLY ADHERED TO DIAPER. Patent dated July 20, 1976. Disclaimer filed Aug. 25, 1978, by the assignee, *Johnson & Johnson*.
Hereby enters this disclaimer to claims 6, 7 and 8 of said patent.

[*Official Gazette October 17, 1978.*]